(12) United States Patent
Wolanske

(10) Patent No.: US 7,449,006 B2
(45) Date of Patent: Nov. 11, 2008

(54) EQUALIZING LUMBAR ORTHOSIS

(76) Inventor: Walter J. Wolanske, 20 Bidwell Pkwy., Buffalo, NY (US) 14222

( * ) Notice: Subject to any disclaimer, the term of this patent is extended or adjusted under 35 U.S.C. 154(b) by 127 days.

(21) Appl. No.: 11/479,145

(22) Filed: Jun. 30, 2006

(65) Prior Publication Data

US 2008/0004557 A1   Jan. 3, 2008

(51) Int. Cl.
*A61F 5/00*    (2006.01)
(52) U.S. Cl. .................. 602/19; 128/100.1; 128/101.1
(58) Field of Classification Search ..... 128/95.1–100.1, 128/101.1; 602/19; 2/311, 312, 321, 322; D24/190; D2/627
See application file for complete search history.

(56) References Cited

U.S. PATENT DOCUMENTS

| | | | | | |
|---|---|---|---|---|---|
| 2,117,309 | A | * | 5/1938 | Fritsch | 602/19 |
| 2,219,475 | A | * | 10/1940 | Flaherty | 602/19 |
| 3,096,760 | A | * | 7/1963 | Nelkin | 128/95.1 |
| 3,926,183 | A | * | 12/1975 | Spiro | 602/19 |
| 3,927,665 | A | * | 12/1975 | Wax | 602/19 |
| 5,599,287 | A | * | 2/1997 | Beczak et al. | 602/19 |
| 7,083,585 | B2 | * | 8/2006 | Latham | 602/19 |

* cited by examiner

*Primary Examiner*—Kim M Lewis
(74) *Attorney, Agent, or Firm*—Phillips Lytle LLP

(57) ABSTRACT

An equalizing back brace (20) is adapted to be worn by a person. The back brace includes a band (21) adapted to encircle the wearer's torso. The band has a rear portion (22) adapted to be positioned proximate the spine of a wearer, has side portions (23, 24) extending away from the rear portion at opposite directions, and has marginal end portions (25, 26) that are adapted to overlap one another proximate the front of such wearer. These marginal end portions are adapted to be selectively secured to one another to complete and close a band which encircles the wearer's torso. Two tightening mechanisms (28, 28') are mounted on the side portions of the band. Each tightening mechanism has an intermediately-pivoted member (29, 29'), has an upper trace (30, 30') secured to the band and engaging an upper marginal end portion of the member, and has a lower trace (32, 32') secured to the band and engaging a lower marginal end portion of the member. A pull strip (35, 35') is mounted on the band, and engages an intermediate portion of the member. The pull strip is adapted to be secured to the associated side portion at any of a plurality of positions relative thereto. Either or both side of the pull strips may be grasped, and pulled away from the rear portion, and secured to the band to selectively tighten the band about the wearer's torso.

10 Claims, 1 Drawing Sheet

EQUALIZING LUMBAR ORTHOSIS

TECHNICAL FIELD

The present invention relates generally to the field of back braces and lumbar orthotic devices, and, more particularly, to an improved back brace that can be quickly and easily tightened, and that automatically equalizes the forces exerted on the upper and lower portion of the brace independently of whether the wearer is standing or sitting.

BACKGROUND ART

Many people suffer from back pain. There are many possible causes of this pain. In some cases, the pain may be reduced or alleviated by a suitable brace or support. Back braces are certainly known.

One such prior art brace is shown in U.S. Pat. No. 7,001, 348. This reference discloses an adjustable back brace with a rear portion, two side portions, and overlapable marginal end portions. Two pull tabs are adjustably mounted on each of the side portions, and are used to selectively tighten upper and lower cords at the rear of the brace. The pull tabs may be operated separately to adjust the cords independently of one another. Thus, it is possible for the upper portion of the brace to be tightened more than the lower portion, and this is further complicated when the wearer stands or sits.

Other details of prior art braces are shown and described in U.S. Pat. Nos. 6,666,838, 6,610,022, 6,213,968 and 6,964, 644. The aggregate disclosures of each of the above-cited patents are hereby incorporated by reference.

DISCLOSURE OF THE INVENTION

With parenthetical reference to the corresponding parts, portions or surfaces of the disclosed embodiment, merely for purposes of illustration, and not by way of limitation, the present invention broadly provides an improved back brace (20) that is adapted to be worn by a person (not shown).

The improved brace includes a band (21) that it adapted to encircle a wearer's torso. The band has a rear portion (22) adapted to be positioned proximate the spine of a wearer, has side portions (23, 24) extending away from the rear portion in opposite directions, and has marginal end portions (25, 26) that are adapted to overlap one another proximate the front of the wearer. These marginal end portions are adapted to be selectively secured to one another such that the closed band will encircle the wearer's torso.

The improved brace includes at least one tightening mechanism (28) mounted on the band. Each tightening mechanism includes an intermediately-pivoted member (29), an upper trace (30) secured to the band and engaging an upper marginal end portion of the member, a lower trace (32) secured to the band and engaging a lower marginal end portion of the member, and a pull strip (35) secured to the band and engaging an intermediate portion of the member. The pull strip (35) is adapted to be secured to the associated band side portion (23) at any of a plurality of positions relative thereto. The pull strip may be grasped, pulled away from the rear portion and secured to the band to selectively tighten and hold the band around the wearer's torso.

In the preferred embodiment, the rear portion (22) is formed of an elastic material. The rear portion may be provided with a pocket (40), and may further include a stiffening insert (41) that is adapted to be received in the pocket. Additional stiffening inserts may be inserted into the side bands, as desired.

In the preferred embodiment, the upper and lower traces (30, 32) are of substantially equal length such that, when the pull strip (35) is tightened, substantially equal tensile forces will be exerted on the upper and lower traces. This condition will obtain independently of the position of the wearer's torso (i.e., whether standing or sitting, etc). In other words, the brace will automatically self-adjust to equalize the trace forces at all permissible positions of the wearer.

In the preferred embodiment, one of the tightening mechanisms is mounted on each of the side portions.

Accordingly, the general object of the invention is to provide an improved back brace.

Another object is to provide an improved back brace that is automatically self-adjusting and force-equalizing in the sense that the upper and lower portions will be placed under equal tensile loads by the simple action of a pulling a pull strip.

Still another object is to provide an improved back brace that will self-adjust to exert substantially equal forces on the upper and lower portions independently of the position of the wearer's torso (i.e., whether standing or sitting).

These and other objects and advantages will become apparent from the foregoing and ongoing written specification, the drawings, and the appended claims.

DESCRIPTION OF THE PREFERRED EMBODIMENTS

Figure 1:
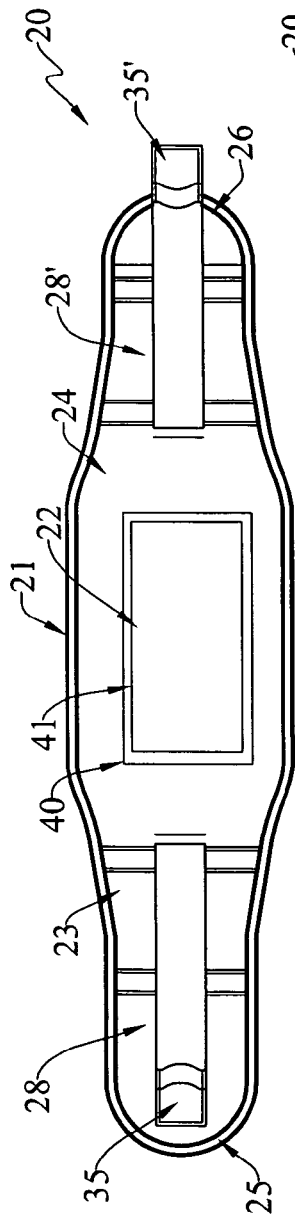
FIG. 1 is a rear elevational view looking at the exterior surface of the improved back brace, in an extended, flat condition, this view showing the left and right pull strips as issuing from slits provided in the rear cover.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 4:
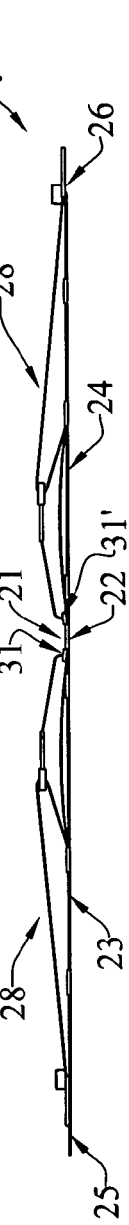
FIG. 4 is a top plan view of the brace shown in FIG. 3.
Figure 3:
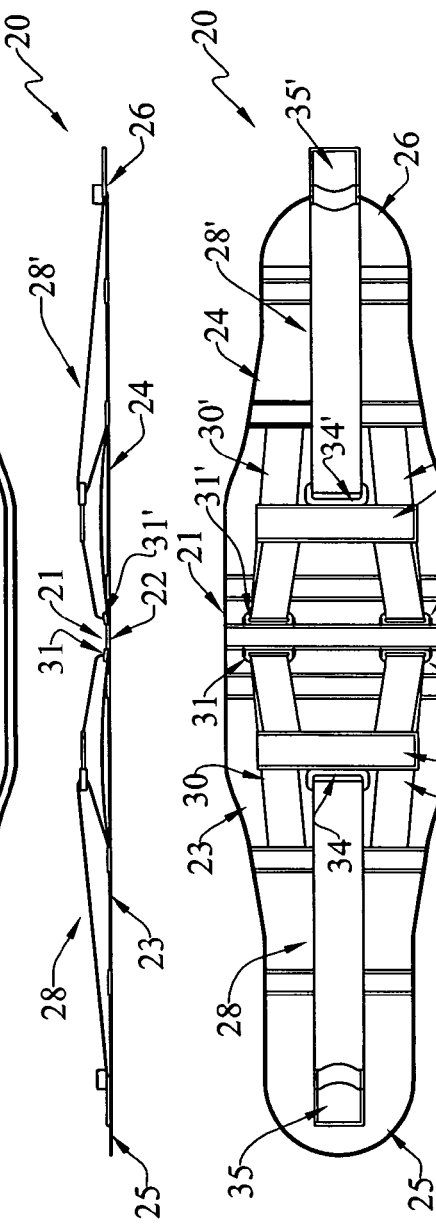
FIG. 3 is a schematic interior view of the brace shown in FIGS. 1 and 2, with the rear cover removed and showing the two tightening mechanisms, and the various members and traces associated therewith.
Figure 2:
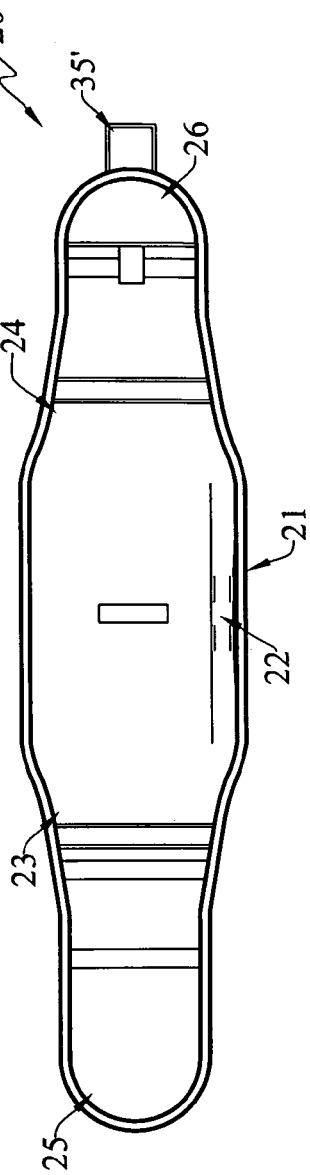
FIG. 2 is a front elevational view looking at the interior surface of the brace shown in FIG. 1.

Referring now to the drawings, and, more particularly, to FIGS. 1-4 thereof, the present invention broadly provides an improved self-adjusting and self-equalizing back brace, of which the presently preferred embodiment is generally indicated at 20.

Brace 20 is adapted to be worn by a person (not shown). The improved brace is shown as including a closable band 21 adapted to encircle a wearer's torso. The band has a rear portion 22 adapted to be positioned proximate the spine of a wearer, and has lateral side portions 23, 24 extending leftwardly and rightwardly, respectively, away from the back portion 21. These side portions terminate in left and right marginal end portions 25, 26, respectively, that are adapted to overlap one another in front of a wearer. These overlapped marginal end portions may be provided with various hook-and-loop fasteners, to secure the band about the torso of a wearer. Other types of fastening devices might be substituted for such hook-and-loop fasteners. Rear portion 22 may be formed of an elastic material that will not gather, if desired.

In the illustrated embodiment, the preferred form is shown as having two tightening mechanisms. The left tightening mechanism is generally indicated at 28, and the right tightening mechanism is generally indicated at 28'. Inasmuch as these two tightening mechanisms are substantially identical, and are arranged as mirror images of one another, only the left tightening mechanism will be explicitly described. The reader will understand that the prime and same reference numeral will refer to the corresponding parts, portions or structure of right tightening mechanism 28'.

Left tightening mechanism 28 is shown as including an intermediately-pivoted member 29. An upper trace 30 in the form a flexible tape, has its left marginal end portion anchored, as by stitching, to an intermediate portion of the left side, has an intermediate portion passed through an eyelet 31 secured to the rear portion 22, and has its other marginal end portion suitably affixed to the upper marginal portion of intermediately-pivoted member 29. Tightening mechanism 28 also includes a lower trace 32 having its left marginal end secured to a lower portion of the band, having an intermediate portion passed through another eyelet 33 attached to the rear portion, and having its other marginal end portion secured to the lower marginal end of intermediately-pivoted member 29. Member 30 also has another eyelet 34 that is positioned on the opposite side of member 29 substantially equally between the points of affixation of the upper and lower traces. A pull strip, generally indicated at 35, has one end secured to the band, has an intermediate portion passed through eyelet 34, and has another marginal end portion adapted to overlay the left band. The facing surfaces of the left band and the pull strip may be provided with a suitable hook-and-loop fasteners such that the wearer need only grab the distal end of the pull strip, and pull it leftwardly, to selectively tighten the brace about his torso, and then reattach it to the band. The back and/or side panels may contain a pocket, such as indicated at 40, into which a stiffening insert 41 may be received.

As noted above, in the illustrated embodiment, there are two such tightening mechanisms. The left tightening mechanism 28 is shown as being operatively associated with the left side portion of the band, and the right tightening mechanism 28' is operatively associated with the right side portion of the band.

One of the principal advantages of the invention is that, because the upper and lower traces are of substantially equal length, the operator need only pull on one or both of the pull strips to tighten the brace about his torso. Such eyelet 34 is located proximate the midpoint of the points at which the upper and lower traces are attached to the intermediately-pivoted member, such tightening of pull strip 35 will cause the tensile forces in the upper and lower traces to be substantially equal to one another. Moreover, the device is somewhat self adjusting in that the intermediately-pivoted member will move or flex appropriately, as the patient stands or sits. The salient feature here is that regardless of the position of the wearer's torso, a tightening of the appropriate tightening mechanism will exert substantially equal forces on the upper and lower traces. Thus, the device is self-equalizing and self-adjusting.

As indicated above, in the preferred embodiment, there are two separate tightening mechanism, one on the left side portion, and the other on the right side portion. These tightening mechanisms may be operated independently or together to affect the desired degree of tightening.

Therefore, while the preferred embodiment of the improved equalizing back brace has been shown and described, and several modifications thereof discussed, persons skilled in this art will readily appreciate that various additional changes and modifications may be made, without departing from the spirit of the invention, as defined and differentiated by the following claims.

What is claimed is:

1. A back brace adapted to be worn by a person, comprising:
   a band adapted to encircle a wearer's torso, said band having a rear portion adapted to be positioned proximate the spine of a wearer, having side portions extending away from said rear portion in opposite directions, and having marginal end portions that are adapted to overlap one another proximate the front of such wearer, said marginal end portions being adapted to be selectively secured to one another such that said band encircles a wearers torso; and
   at least one tightening mechanism mounted on said band, said tightening mechanism having an intermediately-pivoted member, having an upper trace secured to said band and engaging an upper marginal end portion of said member, having a lower trace secured to said band and engaging a lower marginal end portion of said member, said member having an eyelet arranged at an intermediate portion of a longitudinal extent of said member, said tightening mechanism having a pull strip, said pull strip having one marginal end portion secured to said band, and having an intermediate portion passed around said eyelet, said pull strip being adapted to be secured to the associated side portion at any of a plurality of positions relative thereto;
   whereby said pull strip may be grasped, pulled away from said rear portion and secured to said band to selectively tighten said band about said wearer's torso.

2. A back brace as set forth in claim 1 wherein said rear portion is formed of an elastic material.

3. A back brace as set forth in claim 1 wherein said rear portion is provided with a pocket, and further comprising an insert adapted to be received in said pocket.

4. A back brace as set forth in claim 1 wherein when said pull strip is tightened, substantially equal tensile forces will be exerted on said upper and lower traces.

5. A back brace as set forth in claim 4 wherein said member is mounted for movement such that when said pull strip is tightened, substantially equal tensile forces will be exerted on said upper an lower traces independent of the position of said wearer's torso.

6. A back brace as set forth in claim 4 wherein said traces are of substantially equal length.

7. A back brace as set forth in claim 1 and further comprising a hook and loop fastener operatively interposed between said pull strip and said associated side portion for releasably holding said pull strip to said associated side portion.

8. A back brace as set forth in claim 1 wherein one of said tightening mechanisms is mounted on each of said side portions.

9. A back brace as set forth in claim 1 wherein each of said traces has one end fixed to the associated side portion, has an intermediate portion passed through an eyelet arranged proximate said rear portion, and has another end engaging the associated end of said member.

10. A back brace as set forth in claim 1 wherein said pull strip has one end secured to the associated side portion, has an intermediate portion passed through an eyelet arranged between said member upper and lower marginal end portions, and has another end adapted to overlie another portion of said side portion.

* * * * *